(12) United States Patent
Bäck et al.

(10) Patent No.: US 9,381,120 B2
(45) Date of Patent: Jul. 5, 2016

(54) METHOD OF SELECTIVELY ELASTICATING A MOVING WEB AND AN ARTICLE COMPRISING THE ELASTICATED WEB

(75) Inventors: Lucas Bäck, Billdal (SE); Lennart Nilsson, Skärhamn (SE)

(73) Assignee: SCA HYGIENE PRODUCTS AB, Gothenburg (SE)

( * ) Notice: Subject to any disclaimer, the term of this patent is extended or adjusted under 35 U.S.C. 154(b) by 497 days.

(21) Appl. No.: 13/823,188

(22) PCT Filed: Oct. 18, 2010

(86) PCT No.: PCT/SE2010/051123
§ 371 (c)(1),
(2), (4) Date: Apr. 2, 2013

(87) PCT Pub. No.: WO2012/053946
PCT Pub. Date: Apr. 26, 2012

(65) Prior Publication Data
US 2013/0184670 A1      Jul. 18, 2013

(51) Int. Cl.
*A61F 13/00* (2006.01)
*A61F 13/15* (2006.01)
*A61F 13/49* (2006.01)
(Continued)

(52) U.S. Cl.
CPC ..... *A61F 13/15699* (2013.01); *A61F 13/15593* (2013.01); *A61F 13/15723* (2013.01); *A61F 13/496* (2013.01); *A61F 13/49019* (2013.01)

(58) Field of Classification Search
CPC ................. A61F 13/15699; A61F 13/15593; A61F 13/15723; A61F 13/49019; A61F 13/496; A61F 13/15; A61F 13/20; A61F 13/45
See application file for complete search history.

(56) References Cited

U.S. PATENT DOCUMENTS

| 5,830,203 A | 11/1998 | Suzuki et al. |
| 6,391,013 B1 | 5/2002 | Suzuki et al. |
| 7,326,311 B2 | 2/2008 | Krueger et al. |

(Continued)

FOREIGN PATENT DOCUMENTS

| CA | 2716703 A1 | 9/2009 |
| EP | 0 626 161 A1 | 11/1994 |

(Continued)

OTHER PUBLICATIONS

Russian Office Action dated Oct. 3, 2014 issued by the Russian Federation in corresponding Russian Patent Application No. 2013122803 (6 pgs).

(Continued)

*Primary Examiner* — Michael N Orlando
*Assistant Examiner* — Matthew Hoover
(74) *Attorney, Agent, or Firm* — Buchanan Ingersoll & Rooney PC

(57) ABSTRACT

A method for producing an elasticated chassis web for use as a continuous and coherent layer in a disposable garment, including attaching continuous elastic elements (10,11) to a continuous base web (1) along regularly undulating wave-shaped curves (12,13) and cutting out pieces (21) in crotch segments (4) of the continuous base web (1) in order to remove selected parts of the elastic elements (10,11) from the base web (1). A disposable garment made from the elasticated chassis web includes a chassis layer (56) having a hole (69) in a garment crotch portion (43).

15 Claims, 3 Drawing Sheets

(51) Int. Cl.
*A61F 13/496* (2006.01)
*A61F 13/45* (2006.01)

(56) References Cited

U.S. PATENT DOCUMENTS

| | | |
|---|---|---|
| 2006/0064069 A1 | 3/2006 | Rajala et al. |
| 2007/0044608 A1 | 3/2007 | Franke |
| 2010/0069872 A1 | 3/2010 | Lindstöm |

FOREIGN PATENT DOCUMENTS

| | | |
|---|---|---|
| EP | 0688551 A2 | 12/1995 |
| EP | 1 155 668 A2 | 11/2001 |
| EP | 1 300 124 A2 | 4/2003 |
| EP | 1 600 067 A1 | 11/2005 |
| JP | 2003305080 A | 10/2003 |
| JP | 2010082255 A | 4/2010 |
| WO | WO 96/00551 A1 | 1/1996 |
| WO | WO 96/23477 A2 | 8/1996 |
| WO | WO 98/25767 A1 | 6/1998 |
| WO | WO 01/72237 A2 | 10/2001 |
| WO | 2008/115099 A1 | 9/2008 |

OTHER PUBLICATIONS

The extended European Search Report issued on Dec. 9, 2014, by the European Patent Office in corresponding European Application No. 10858722.1-1308. (6 pages).
International Search Report (PCT/ISA/210) issued on Jun. 20, 2011, by the Swedish Patent Office as the International Searching Authority for International Application No. PCT/SE2010/051123.
Written Opinion (PCT/ISA/237) issued on Jun. 20, 2011, by the Swedish Patent Office as the International Searching Authority for International Application No. PCT/SE2010/051123.
Written Opinion of the International Preliminary Examining Authority(PCT/IPEA/408) issued on Dec. 4, 2012, by the Swedish Patent Office as the International Searching Authority for International Application No. PCT/SE2010/051123.

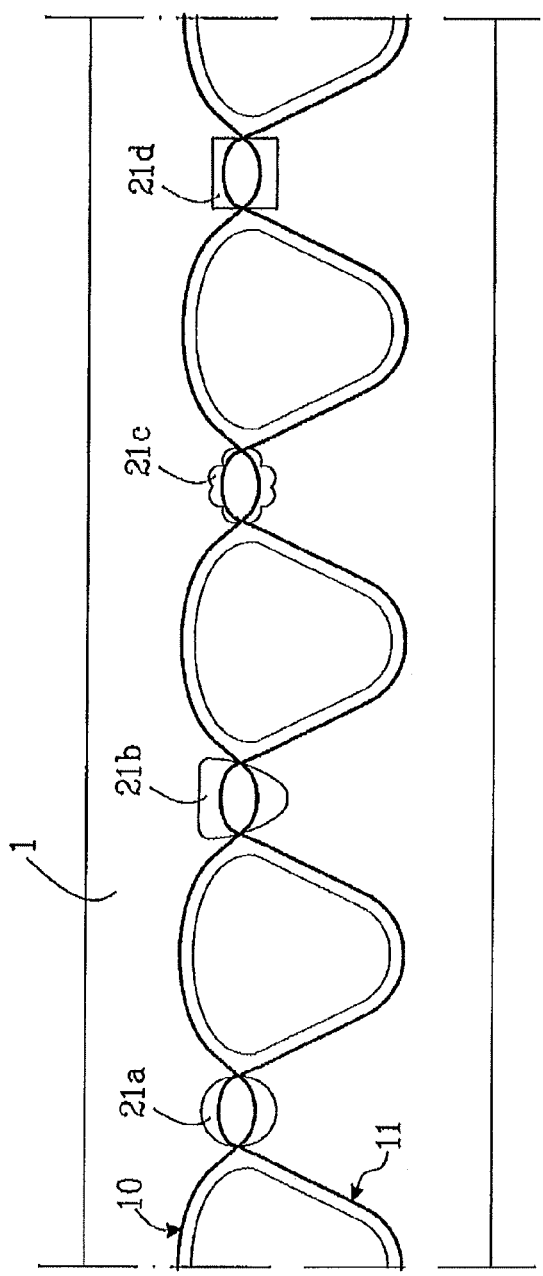
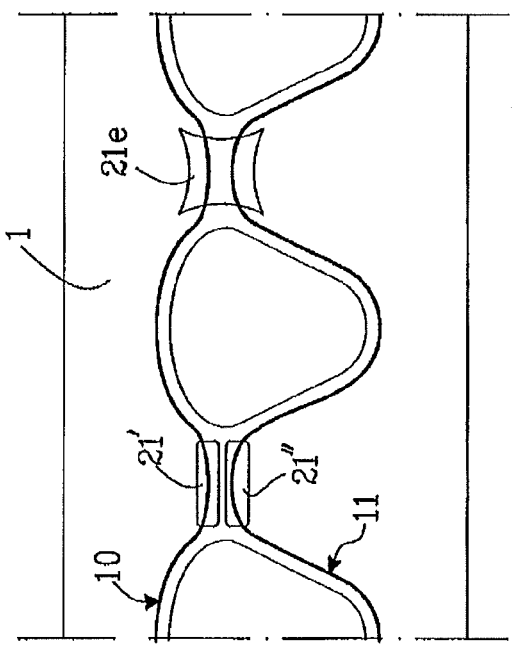
Fig.2
Fig.3

METHOD OF SELECTIVELY ELASTICATING A MOVING WEB AND AN ARTICLE COMPRISING THE ELASTICATED WEB

TECHNICAL FIELD

The invention pertains to a method for producing an elasticated chassis web for use as a continuous and coherent supporting layer in a disposable garment and to a disposable garment comprising the chassis web.

BACKGROUND OF THE INVENTION

When designing disposable garments for wearing about the lower trunk such as disposable pants, disposable diapers and pant diapers it has become increasingly more important that the articles closely resemble regular underwear in appearance and comfort. For this reason it is necessary for the manufacturers to carefully tailor the articles to optimise fit and comfort. In order to fit snugly around the lower torso, the absorbent articles are provided with elastic elements arranged around contoured leg openings formed by making cut-outs in the garment material.

A major concern when producing disposable garments such as disposable pants, diapers, pant diapers, and the like, is to keep the manufacturing costs as low as possible while providing products with high functionality and an appealing finish. To keep costs at a minimum, high production speeds and little material waste are desirable features of the production method.

The problem of applying elastic elements intermittently and in a nonlinear configuration at the leg edges of an absorbent article has been addressed in U.S. Pat. No. 7,326,311 B2 and in International Patent Application WO 98/25767 A1. The methods disclosed in U.S. Pat. No. 7,326,311 B2 and WO 98/25767 A1 involve making an elastic laminate by attaching a continuous elastic element in a curved pattern on a supporting web and dividing the supporting web in two halves each carrying discrete portions of the elastic element. The two parts of the supporting web are then introduced in a process for longitudinal production of absorbent articles and are attached along the side edges of a production web with the elastic portions forming leg elastic in the finished product.

Although allowing leg elastic to be incorporated in an absorbent article in a fairly simple manner, the methods in U.S. Pat. No. 7,326,311 B2 and WO 98/25767 A1 both require additional material for carrying the elastic element to be introduced in the manufacturing process. As the supporting webs have no function in the finished product but are merely a means for handling the elastic elements in the process, the supporting webs add unwanted cost to the absorbent article and entail excess material consumption which is negative for environmental reasons. When making disposable absorbent articles, the manufacturers are highly concerned to keep the use of materials to a minimum in order to reduce the carbon footprint of the disposable absorbent article.

A common way of forming disposable garments such as pants, diapers and pant diapers is by a cross direction production method where the webs and components forming the garments are moved along a production path parallel with the cross direction of the garments. As the leg edges of a pant-type garment extend generally in the longitudinal direction of the garment transverse to the machine direction, cross-direction production commonly involves applying continuous pre-stretched leg elastic elements along two curvilinear paths extending in the machine direction to form a front half leg elastic and a rear half leg elastic. Continuous application of the elastic elements is preferred, as it allows for higher production speeds than methods involving application of discrete elastic pieces. However, one problem with continuous elastic application in cross direction production is that the leg elastic elements will also extend across the crotch portions of the finished disposable garments. The pre-stretched elastic elements in the crotch portions cause the crotch portion material to contract and deform, giving rise to unwanted corrugations that apart from detracting from the underwear-like appearance of the garment can act as channels in which liquid may flow out of the disposable garment. For these reasons, it is normally preferred if the elasticity in this area can be removed or neutralised.

International Patent Application WO 01/72237 A2 discloses a cross direction type method for applying leg elastic along leg openings in pant type diapers. The method involves adhesively attaching elastic elements in a semicircular pattern along first and second parallel travelling webs having inner edges facing each other. The webs and the elastic elements are then covered by a covering web to form two parallel elastic laminates. The inner edges of the elastic laminates are trimmed off, at the same time removing parts of the elastic elements that would otherwise have extended across the crotch portions of the assembled pant diapers. The two parallel laminates having the leg elastic elements captured between the layers of the laminates are then again covered by a covering web to form a continuous elasticated chassis web that may be further processed into pant diapers by adding waist elastic, absorbent cores, cutting out leg openings, forming side joins, etc.

The method of removing elastic elements from the crotch portions of pant garments as disclosed in WO 01/72237 A2 suffers from the same major drawback as the methods disclosed in U.S. Pat. No. 7,326,311 B2 and WO 98/25767 A1 in that additional material is needed for carrying and supporting the elastic elements in the process.

A further attempt at solving the problem with unwanted elastication in the crotch portion of a disposable pant garment is found in International Patent Application WO 96/23477. The method in WO 96/23477 involves causing the elastic elements to be present in the crotch portion of the produced garments "in a substantially relaxed state". This is accomplished by severing the elastic elements in the crotch portions, or by applying the stretched elastic in a non-bonded curve and allowing the elastic to relax and assume a non-curved shape.

One disadvantage with the method according to WO 96/23477 is that it may be difficult to synchronize the additional relaxation step to be performed at the correct positions along the production web. Furthermore, as the method requires a separate relaxation step it will complicate the production process with the risk of causing a reduction in speed and an increase in faulty products. A major disadvantage of the method WO 96/23477 is that the end product will still have elastic elements present in the crotch portion of the product. This is highly undesirable both for comfort reasons and for the reason that the elastic elements diminish the undergarment-likeness of the finished disposable pant garment.

WO 96/00551 discloses a diaper produced from a continuous web and having elastic elements that have been deactivated mechanically or by other means such as chemically or by applying heat in areas of the elastic elements crossing the crotch portions of the diapers. The production method in WO 96/00551 suffers from the same problems as the method in WO 96/23477 in that it requires a deactivation step and in that the deactivated elastic elements remain in the crotch portions.

One objective of the present invention is therefore to offer a simplified and more efficient manufacturing method for the production of disposable pant garments. A further object of the invention is to reduce waste of covering materials when producing disposable pant garments. A still further objective is to provide a low-cost yet highly functional, comfortable and selectively elasticated disposable article.

SUMMARY OF THE INVENTION

In accordance with the invention, there is provided an improved method for producing an elasticated chassis web for use as a continuous and coherent layer in a disposable garment, comprising the steps of:
  a) feeding a continuous base web along a production path in a machine direction, MD, the continuous base web having a cross machine direction, CD, transverse to the machine direction, MD, and parallel side edges in the machine direction and having leg edge segments and crotch segments extending in the cross machine direction, CD, and alternating in the machine direction, MD;
  b) stretching first and second continuous elastic elements;
  c) feeding said first and second continuous elastic elements in said machine direction, MD, along first and second regularly undulating wave-shaped curves, said curves having equal wave length, $£$, and having wave crests directed towards said side edges of said continuous base web and wave troughs directed away from said side edges of said continuous base web, said wave crests and wave troughs of said first wave-shaped curve being in register with said wave crests and wave troughs of said second wave-shaped curve with said elastic elements being at a maximum distance from each other within said leg edge portions of said continuous base web and with said elastic elements being at a minimum distance from each other within said crotch segments of said continuous base web;
  d) attaching said first and second stretched elastic elements to said continuous base web along said first and second regularly undulating wave-shaped curves in said leg edge segments and said crotch segments;
  e) forming cut-out pieces of said continuous base web in said crotch segments,
  f) simultaneously forming cut-off crotch pieces of said stretched elastic elements being attached to said cut-out pieces of said continuous base web; and
  g) creating holes in said crotch segments of said continuous base web by removing said cut-out pieces from said continuous base web together with said cut-off crotch elastic pieces.

The method of the invention involves cutting out and completely removing pieces of the crotch segments of the base web together with parts of the leg elastic elements that would otherwise have remained extending across the crotch segments. The cut-off pieces of the elastic elements are attached to the cut-out pieces of the base web and will be removed from the base web when removing the cut-out pieces. In this way, the cut-away elastic pieces can be safely and easily disposed of in a controlled manner without leaving free cut-off segments of elastic that have to be removed by special suction means. If not properly taken care of and removed from the production web, free segments of elastic elements may interfere with the manufacturing process by getting caught in the production equipment or by being unintentionally incorporated between layers in the assembled product.

By means of the invention, unwanted crotch elastic may be selectively removed by a cutting unit that is already present in the production line. Accordingly, there is no need for a separate strip cut unit as is used for the support webs for the elastic elements of the prior art which means that the machine construction is simplified and the risk of technical failure is reduced. Moreover, in comparison with the prior art using separate elastic supporting webs for removal of unwanted elastic segments, material waste is greatly reduced with the method according to the invention as no additional material layers are needed to support the cut-away elastic elements. A further advantage of the invention is that even after forming leg openings in the basis web, the chassis web which forms a support structure for all other components of the pant garment is a single coherent web which is held together by connecting strips that are left extending in the CD on either side of the crotch holes, between the crotch holes and leg openings that may be formed in the basis web. Hence, in accordance with the invention there is only one chassis web that needs to be guided and synchronized with other components in the production process.

The first and second stretched elastic elements may be attached to said continuous base web by means of adhesive or in any other suitable manner such as by means of thermowelding or ultrasonic welding. Adhesive may be applied as a continuous or pattern coating on the continuous base web or may be applied to the elastic elements or both to the elastic elements and to the base web. By way of example, the adhesive may be applied to the continuous base web in first and second attachment areas generally coinciding with the first and second regularly undulating wave-shaped curves. Any suitable method may be used to apply the adhesive such as spraying, extruding, slot-coating, gravure coating, meltblowing, etc.

The first and second stretched elastic elements may be covered by a covering web which is attached to the continuous base web and serves to firmly hold the elastic elements in the desired curve shape. The covering web may be a nonwoven material, a film, a scrim, or other flexible web material. Laminates of one or more layers of material may also be used.

The holes in the continuous base web may be covered by a crotch material that is attached to the continuous base web after cutting out and removing the cut-out pieces from the continuous base web.

The crotch material may be in the form of discrete pieces of material that are applied intermittently to the moving continuous base web.

Alternatively, the crotch material may be in the form of a continuous web. If the crotch material is in the form of a continuous web, it must be applied before making leg cut-outs in the continuous base web.

The crotch material has a first surface facing the continuous base web and a second surface facing away from the continuous base web. The first surface may be formed from a nonwoven material.

In the finished disposable pant garment, the base web will generally be placed on the outside of the pant garment chassis and will form a major part of the outer surface of the garment. The supplementary crotch material will be applied on the inner, wearer-facing side of the base web and will be exposed through the hole in the base web that is formed when the crotch piece is removed from the base web such that it can be seen and touched from the outside of the pant garment.

The supplementary crotch material may be similar in colour and texture to the base web material to camouflage the contours of the hole in the base web. Alternatively, the crotch material may be selected to provide a contrast to the base web material such that it can be identified visually and/or by touching the material. To this end, one or more of colour, texture, gloss or type of material may differ between the crotch material and the base web. A contrasting crotch material may be used as an aid for proper positioning of the pant garment, for identification of what is the front and the back of the garment, for providing wetness indication or as a decorative feature to increase the underwear-like appearance of the disposable pant garment. A crotch material that differs in tactile properties from the surrounding chassis material may be particularly useful when changing the disposable garment in poor light such as at night. A transparent material, such as a transparent plastic film or viewing window may be used to provide a visual indication of wetness in an absorbent disposable garment. The crotch material may also provide sensory wetness indication. Liquid that has been absorbed in the garment will make a plastic film feel warmer or colder than a surrounding material such as a thicker film material or a material with better isolating properties such as a nonwoven or a porous film or foam material. The crotch material may further be used to provide decoration, size indication, an indication of the gender of the intended wearer, etc.

The intermittently elasticated base web according to the invention may be further processed by forming leg openings in the leg edge segments of the continuous base web. The leg openings may be formed either before or after application of a supplementary crotch material. If the supplementary crotch material is applied as a continuous web, the leg openings must be formed after application of the supplementary crotch material. If the supplementary crotch material is applied intermittently as discrete pieces of material, the leg openings may be formed before or after application of the supplementary crotch material as found suitable.

The cut-out pieces may be formed by means of any cutting method known in the art such as water jet or laser cutting. A particularly suitable means of forming the cut-out pieces is by using a rotary die cutter (RDC) as is well known in the art. An RDC comprises a rotating cutting roll having cutting edges on the peripheral surface. The cutting roll works against an anvil roll and continuously cuts a web in the nip between the rolls.

When using an RDC, the same rotating cutting roll may be used to form both the cut-out pieces in the crotch segments of the base web and leg openings. In this way the length of the machine may be considerably reduced as compared to a machine having separate cutting rolls for the leg cut-outs and the crotch cut-outs. A suitable cutting roll may have a circumference corresponding to two leg cut-outs and two crotch cut-outs, equaling the length of two products. However, other cutting roll sizes may be used as found suitable.

The supplementary piece of crotch material may be comprised in a core pack which is a prefabricated component comprising a topsheet layer, a backsheet layer and an absorbent core between the topsheet layer and the backsheet layer.

The method according to the invention may further include applying waist elastic along at least one of the side edges of the continuous base web. The waist elastic may be intermittently applied but is preferably applied continuously along one or both side edges. The method may also include application of body elastic between the leg elastic curves and the waist elastic.

The continuous base web may be further processed by being folded along the longitudinal centre line of the base web and by connecting the two halves of the base web in edge seams formed in the cross machine direction, CD, centrally across each wave crest segment and subsequently cutting the continuous base web into individual pant garments in the cross machine direction by cutting through the edge seams.

The edge seams may be permanent edge seams, openable edge seams, or openable and reclosable edge seams, as known in the art. A continuous base web in accordance with the invention may also be used to produce open pant garments, such as open diapers that are provided with closure means such as fastening tabs for fastening the garment around the waist of a wearer.

The invention also relates to an improved disposable pant garment having front and rear waist edges and leg edges, a front body portion, a rear body portion and a crotch portion between the front and rear body portions and comprising a coherent chassis layer extending continuously from the front waist edge to the rear waist edge and having elastic elements attached along said leg edges and along at least one of said front and rear waist edges, the crotch portion having a hole occupying an area of the crotch portion in the chassis layer, the area of the hole being delimited by a hole periphery, wherein the elastic elements that are attached along the leg edges terminate at the hole periphery with no part of the elastic elements extending from the hole periphery into the area of the hole.

The disposable pant garment according to the invention may be an absorbent pant garment.

The absorbent pant garment may comprise a core pack arranged in the crotch portion, the core pack comprising a topsheet layer, a backsheet layer and an absorbent core arranged between the layers.

The pant garment may be a pant diaper having closed side seams connecting the front body portion with the rear body portion to form a panty having leg openings and a waist opening.

When cutting away the unwanted parts of the elastic elements from the base web the cut-out crotch piece and the resulting hole may have any suitable shape such as circular, square, oval, T-shaped, mushroom-shaped, heart shaped, etc. The only requirement is that all unwanted elastic is removed from the base web. Moreover, the holes should preferably be arranged with MD spacing between the crotch holes and leg openings that are cut out in the base web. A suitable spacing between leg openings and crotch holes should be in the order of 10-80 millimeters, preferably 20-50 millimeters.

DEFINITIONS

As used herein a "pant garment" or "pant type garment" is any type of garment that is worn in a pant-like fashion around the lower trunk of a user's body. The pant garment may be a pair of disposable, non-absorbent underpants that may be worn with or without an absorbent insert. Other disposable articles that are considered to be pant garments are disposable absorbent sanitary pants and pant diapers and open diapers and diaper covers having fastening means for fastening the diaper or diaper cover in a pant-like configuration on a user's body.

A garment chassis as used herein is a coherent structure with a main function of supporting and connecting garment components such as elastic elements and absorbent components.

The outer side or outer surface of the base web or garment is the side or surface of the web or a garment made from the web that is intended to be facing away from a wearer of the garment when the garment is being worn.

The inside or inner surface of the base web or a garment made from the web is the side or surface of the web or garment that is intended to be facing towards a wearer of the garment when the garment is being worn.

A "layer" or a "web" as used herein is a generally two-dimensional structure that may comprise one or more plies and may be in the form of a laminate made from plies of the same or different materials.

An "elastic" material as used herein is to be understood in the conventional way as being a material that after stretching resiliently returns to a less extended state, ideally to its original, unstretched state.

By an elongated elastic means of the invention being "continuously attached" along a segment thereof is meant that the elastic means is bonded to a base web with sufficiently closely spaced bonds to maintain a functional curvature of the elastic means after attachment to the base web. Consequently, a continuous attachment may be achieved by closely spaced intermittent bonds, such as bonds with a maximum spacing along the elongated elastic means of 7 mm or by a true continuous bond extending unbroken over the full length of the continuously attached segment of the elastic means.

By "snap back" as used herein is meant the sudden and vigorous relaxation and retraction of a tensioned elastic element that takes place when the tensioned elastic element is severed.

BRIEF DESCRIPTION OF THE DRAWINGS

The invention will be described in greater detail below with reference to the figures shown in the appended drawings.

FIG. 2 shows examples of elasticated base web cut-outs;

FIG. 3 shows further examples of elasticated base web cut-outs; and

DETAILED DESCRIPTION OF EMBODIMENTS

Figure 1:
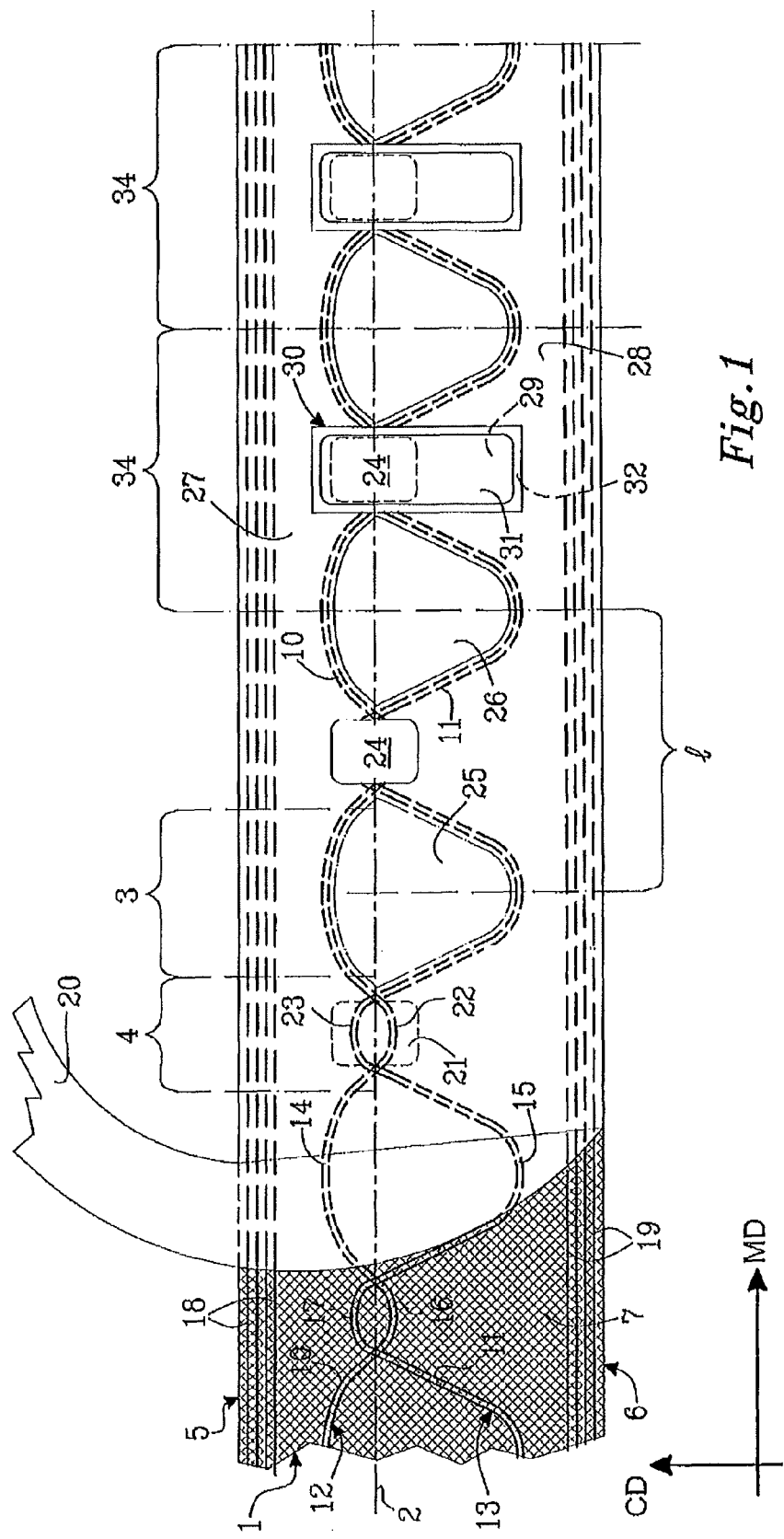
FIG. 1 shows an elasticated base web according to a first embodiment of the invention.

The base web 1 for production of a disposable pant-shaped garment that is schematically shown in FIG. 1 is continuously moved in a machine direction, MD and has a cross machine direction, CD, perpendicular to the MD. The base web 1 has a longitudinal crotch centre line 2 in the MD and is divided in the CD into leg edge segments 3 and crotch segments 4 extending transversely across the base web 1 in the CD, and arranged in alternating sequence in the MD. The base web 1 has first and second parallel side edges 5, 6 in the MD. The crotch centre line 2 is a line extending in the MD of the base web 1, between the side edges 5,6 of the base web 1. In the base web 1 shown in FIG. 1, the crotch centre line 2 is offset in the CD towards the side edge 5, shown at the upper part of the drawing. The crotch centre line 2 will usually be offset towards the side edge of the continuous base web 1 that will be placed at the front waist edge of the finished pant garment. Other configurations such as base webs having the crotch centre line coinciding with the MD centre line of the base web, or base webs having the crotch centre line offset towards the side edge that will be placed at the rear waist edge of the finished pant garment are also contemplated within the scope of the invention.

The base web 1 can consist of any flexible web material as commonly used in the art, such as a layer of nonwoven material, a plastic film or a laminate of two or more sheets of the same or different materials. The base web 1 may be elastic or inelastic and will preferably comprise or consist of at least one nonwoven layer. Suitable nonwoven materials are carded bonded nonwovens, spunbond nonwovens, spunlaced nonwovens, meltblown nonwovens, etc. The nonwoven webs may comprise or consist of thermoplastic fibres. The base web according to the invention will form part of a chassis for a disposable pant-type garment and is commonly incorporated in joins in the garment. For this reason, it is highly desirable that the base web comprises thermoplastic material and is weldable by heat or by ultrasonic welding processes. Examples of suitable polymers for use in the base webs according to the invention are polyethylene, polyesters, polypropylene and other polyolefin homopolymers and copolymers. A weldable nonwoven web preferably has a high content of thermoplastic fibres and may contain at least 50% thermoplastic fibres and preferably at least 80% thermoplastic fibres.

The base web 1 is coated with an adhesive 7, such as a hot melt adhesive that is applied to the base web 1. Adhesive may be applied as a continuous or pattern coating on the continuous base web by any suitable method such as spraying, slot coating, gravure printing, meltblowing, etc. The adhesive may be uniformly distributed over the surface of the base web or may be applied with different amounts in different areas. It may in particular be desirable to use more adhesive or a stronger adhesive in areas of the base web to which elastic elements are to be attached than in areas of the base web where the adhesive merely serves to join the base web 1 with other web materials.

As the base web 1 is moved in the MD, first and second continuous leg elastic elements 10,11 are stretched and attached in the stretched state to the base web 1. Typical stretch rates are around 200% which means that the elastic elements have been stretched to a length of three times their original unstretched length. Lower or higher stretch rates may be used as desired within the scope of the invention. The leg elastic elements 10,11 may be stretched to different degrees, resulting in a finished pant garment having differently tensioned front and rear parts of the leg elastic.

The leg elastic elements 10,11 will form leg elastic in an assembled disposable pant garment and may be in the form of elastic threads or bands. Each leg elastic element 10,11 may consist of one or more strings or bands of elastic material such as natural or synthetic rubber, elastic foam, elastic film, elastic nonwoven, etc. Elastic strings may have an outer layer of inelastic textile threads spun around an elastic core.

The first and second continuous leg elastic elements 10,11 are fed in the MD along first and second regularly undulating wave-shaped curves 12,13 and are attached to the adhesive coating 7 on the base web 1. Depending on the desired shape of the leg elastic in the finished pant garment, the first and second curves 12, 13 may have other shapes than those shown in FIG. 1. The curves may have the same shape or may have different shapes as in FIGS. 1-3 and may be overlapping in the crotch segments 4 as shown in FIGS. 1 and 2 or be placed at a distance from each other in the crotch segments 4 as shown in FIG. 3. It is common that the leg openings in a pant garment have different curvatures in the front half and in the rear half of the garment in order to obtain better anatomical fit. However, the first and second curves 12,13 must always have equal wave length, l, and have wave crests 14,15 directed towards side edges 5,6 of the base web 1 and wave troughs 16,17 directed away from the side edges 5,6 of the base web 1. Accordingly, for each curve 14, 15, the wave crests are those parts of the curve that are closest to a side edge 5,6 of the base web 1 and the wave troughs are those parts of the curve that are furthest away from that side edge 5,6 of the base web 1. The wave crests 14 and wave troughs 16 of the first wave-shaped curve 12 are arranged in register with the wave crests 15 and wave troughs 17 of the second wave-shaped curve 13. Accordingly, the leg elastic elements 10,11 are attached to the base web 1 at a maximum distance from each other within the leg edge segments 3 of the base web 1 and at a minimum distance from each other within the crotch segments 4.

In a garment made from the elasticated base web 1, the leg edge segments 3 of the base web 1 are portions of the web that will form or be part of side portions of the garment. These portions will have leg openings encircled by leg elastic elements and will be placed over a user's hips when the garment is being worn. The crotch segments 4 are portions of the web that will form a component of the garment's crotch portion and will be located centrally between the side portions. When the garment is worn, the crotch portion is placed in the user's crotch. If the pant garment is an absorbent garment an absorbent core will be placed in the crotch portion of the garment.

In the embodiment shown in FIG. 1, the first and second stretched leg elastic elements 10,11 are attached to the base web 1 by means of adhesive that has been applied to the base web 1 and optionally also to the elastic elements. However, other means of attachment such as ultrasonic or thermal welding or adhesive applied in a contoured pattern following the elastic curves or directly to the elastic elements are contemplated within the scope of the invention.

Waist elastic elements 18,19 are applied along each side edge 5,6 of the base web 1. The waist elastic elements 18,19 are shown in FIG. 1 as multiple continuous elastic strands extending parallel to each other at the side edges 5,6 of the base web 1. In the FIG. 1 embodiment, the waist elastic elements 18,19 are attached in a tensioned state directly to the adhesive 7 that is applied to the base web 1. Alternatively, waist elastic may be provided in the form of a waist band formed from plies of substantially non-elastic nonwoven material that is elasticized by one or more elongate elastic members, such as elastic threads or bands that are arranged between the plies. The plies can be formed from a single layer of material such as an edge portion of the base web 1 or a particular waistband web that is folded over onto itself or can be made from separate materials that are laminated together with the elastic elements therebetween. The waistband may further comprise or consist of elastic web material such as elastic foam, film or nonwoven. An elastic waistband may be provided as a prefabricated component that is attached to the side edges 5,6, of the base web 1. The elastic elements may be made of material that is stretched and attached in a tensioned or non-tensioned state to supporting elastic or inelastic webs. An elastic material that is attached to an inelastic web in a non-stretched state will have to be treated in order to activate the elasticity. Activation may be made by mechanical, thermal or chemical means or by irradiation. The waist elastic is an optional component of the invention and may be omitted if desired. If waist elastic is provided it may be provided in a different way from that shown in FIG. 1. Accordingly, the waist elastic may be arranged along only one of the side edges of the base web 1 or may be intermittently applied as discrete segments of elastic along one or both side edges 5,6.

The waist elastic elements 18,19 in FIG. 1 are shown to be arranged only in the vicinity of the side edges 5,6 of the base web 1. Further elastic elements may be placed in the area between the leg elastic elements 10,11 and the waist elastic elements 18,19. Such elastic elements would form body elastic in a finished pant garment.

After application of the elastic elements 10,11,18,19 to the base web 1, the elastic elements 10,11, 18,19 are covered by a covering web 20 that is laminated to the base web 1 so that all elastic elements are sandwiched between the base web 1 and the covering web. The covering web 20 serves to lock the leg elastic elements 10,11 in the desired curve shape and to ascertain that the elastic elements are held securely in a tensioned state. In the example shown in FIG. 1, the covering web 20 is attached to the base web 1 by means of the adhesive 7 that has been applied to the base web 1. Other ways of attaching the covering web 20 to the base web 1 are ultrasonic welding, thermowelding and needling. Adhesive attachment of the elastic elements may be supplemented by further attachment means to form additional bonds between the base web and the covering web. The covering web may be chosen from the same materials as the base web with nonwoven materials being preferred as covering webs.

After application of the covering web 20 to the base web 1, crotch cut-out pieces 21 are cut out from the crotch segments 4 of the base web 1. The crotch cut-out pieces 21 consist of a portion of the base web 1, portions of the first and second leg elastic elements 10,11 and a portion of the covering web 20. Accordingly, simultaneously with forming the crotch cut-out pieces 21, cut-off segments 22,23 of the stretched elastic elements 10,11 that are attached to the crotch cut-out pieces 21 are created.

The cut-out crotch pieces 21 are subsequently removed from the base web 1 together with the cut-off crotch elastic segments 22,23. In this way, holes 24 are created in the crotch segments 4 of the continuous base web. In FIG. 1, the cut-out crotch pieces 21 and the holes 24 are shown to have a rectangular shape with rounded corners. However, as shown in FIGS. 2 and 3, the cut-out piece 21*a-e* may have any suitable shape as long as the portions of the leg elastic elements 10,11 that are to be removed from the base web 1 are located inside the contour of the cut-out piece 21. Accordingly, the cut-out-piece may be circular, triangular, heart-shaped, flower-shaped, square, etc. As is illustrated in FIG. 3, separate cut-out pieces 21', 21" may be formed for each leg elastic element 10,11.

Leg cut-outs 25 are formed between the leg elastic elements 10,11 in the leg edge segments 3 of the base web 1. After removal of the leg cut-outs 25, the base web is provided with leg openings 26. Removal of the cut-out crotch pieces 21 and the leg cut-outs 25 may be carried out in any suitable way such as by using suction means.

The base web 1 will constitute a continuous chassis layer in the pant garment and the material remaining on each side of the crotch holes 24 between each crotch hole 24 and the adjacent leg openings 25 on either side of the hole 24 will connect a front body portion 27 of the chassis layer with a rear body portion 28 of the chassis layer.

For the production of most pant-type garments, the hole 24 in the crotch segment 4 needs to be supplemented with a material replacing the material that was cut away from the crotch segment 4 when removing the crotch elastic segments 21,22. The supplementary material may be a nonwoven material, a plastic film, a nonwoven/film laminate or a core pack 29 as shown in FIG. 1. The supplementary material may be applied on the outer side of the base web to create a smooth outer surface in the crotch portion of the finished pant garment. The outer side of the base web or garment is that side or surface that is intended to be facing away from a wearer of the garment when the garment is being worn. However, for some applications it may be preferred to apply a supplementary material to the inner, wearer-facing side of the base web 1 or to both the inner side and the outer side of the base web 1. For other applications such as when producing pant garments intended for use together with a separate absorbent insert the supplementary material may be omitted.

A supplementary crotch material that is applied on the inner, wearer-facing side of the base web will be exposed through the crotch hole 24 in base web such that it can be seen and touched from the outside of the finished pant garment.

As disclosed herein, the supplementary crotch material may be similar in colour and texture to the base web material to camouflage the contours of the hole in the base web. Alternatively, the crotch material may be selected to provide a contrast to the base web material such that it can be identified visually and/or by touching the material.

In a finished pant garment, the supplementary material can be configured to define the width of the crotch portion between the leg openings 26 formed by removing the leg cut-outs 25. The supplementary material may have curved or straight edges in the CD, i.e. in the longitudinal direction of the assembled pant garment. By attaching supplementary crotch material over the holes 24 in the crotch segments 4 of the base web 1 before making the leg cut-outs, the edges of the supplementary material may be given a desired curvature following the curvature of the leg cut-outs 25 in the crotch segments 4. In such embodiments the supplementary material may be attached over the crotch holes 24 as a continuous web of material or as intermittently applied discrete pieces of material.

The holes 24 in the crotch segments 4 may be cut in the same step as the leg cut-outs, such as by using a single rotary die cutter or may be formed in a step separate from the formation of the leg cut-outs 25. A single RDC may be preferred for reasons of process economy as it simplifies the machine construction. On the other hand, by making crotch holes 24 separately before making the leg cut-outs 25, the crotch holes 24 may be covered by a supplementary material before the leg cut-outs 25 are formed. In this way the stability of the base web 1 may be increased which may be an advantage in the further processing of the web.

When applying a supplementary material after leg cut-outs 25 have been made in the base web 1, the supplementary material must be in the form of discrete pieces of material.

In the process shown in FIG. 1, a core pack 29 is attached over the crotch hole 24 in the base web 1. A "core pack", as used herein is a separately produced component that is integrated with the base web 1 and includes an absorbent core 30 enclosed between a topsheet 31 and a liquid impermeable backsheet 32. The core pack 29 may be attached by any suitable means such as by adhesive or thermo bonding or ultrasonic bonding. Although the core pack 29 is shown in FIG. 1 to have a rectangular shape, the core pack may take other forms such as hourglass shape, trapezoidal shape, etc.

The various components included in the core pack 29 can be connected to one another in a conventional manner, for example by adhesive bonding, ultrasonic bonding or thermobonding. The core pack can of course contain further components in addition to those described here, such as a liquid transport sheet, elastic members, shape-stabilizing members, shaping elements, side barriers, etc.

The liquid-permeable topsheet 31 can consist of any material known for the purpose, such as a layer of nonwoven material, a perforated plastic film, net material, tow, or the like. The topsheet can, of course, also consist of a laminate of two or more sheets of the same or different material.

The liquid-impervious barrier sheet 32 can consist of a liquid-impermeable plastic film, a nonwoven sheet which has been coated with a liquid barrier material, or some other flexible material sheet which has the ability to withstand liquid penetration. However, it may be advantageous if the liquid-impervious barrier sheet has some degree of breathability, i.e. permits the passage of water vapour through the sheet.

The absorption core 30 can be made up of absorbent material, such as cellulose fluff pulp, tissue, absorbent foam, etc. It is also possible for the absorption core to contain superabsorbents, i.e. polymer materials which are able to absorb body fluid corresponding to many times their own weight and form a hydrogel. Such superabsorbents are usually present in the form of particles, but fibres, flakes, granules and films are also available. Moreover, the absorption core can comprise non-absorbent components such as stiffening elements, shaping elements, binders, etc. Various types of liquid-receiving porous structures such as fibre waddings, open-cell foam or the like can also be included in the core.

After all components have been added to the base web 1, the base web 1 is folded centrally in the machine direction MD, side seams are formed in the CD between garment sections 34 to join the front and rear body portions 27,28 of the garment sections 34. Subsequently, the garment sections 34 are cut off from the continuous base web 1 by cutting through the side seams in the cross machine direction, CD, so that individual pant garments are formed.

Side seams are often arranged in a pant garment to connect the front body portion to the rear body portion and to form a pant having a waist opening and leg openings. The side seams are intended to be arranged at the user's hips during use of the disposable pant, The side seams are preferably designed so that they can withstand the tensile forces which arise when the pant is being put on and is being worn, but such that they can be torn apart or opened in a controlled manner when the disposable pant is taken off or to check if the pant needs changing. In the latter instance, the side seams are preferably reclosable seams, as known in the art. Side seams may be formed by any suitable means known in the art such as adhesively, by ultrasonic bonding, by thermobonding or by stitching or needling. As the person skilled in the art is well aware, if thermobonding or ultrasonic bonding is being used, the base web material needs to comprise a sufficient amount of thermoplastic material in order to obtain sufficient bond strength.

Figure 4:
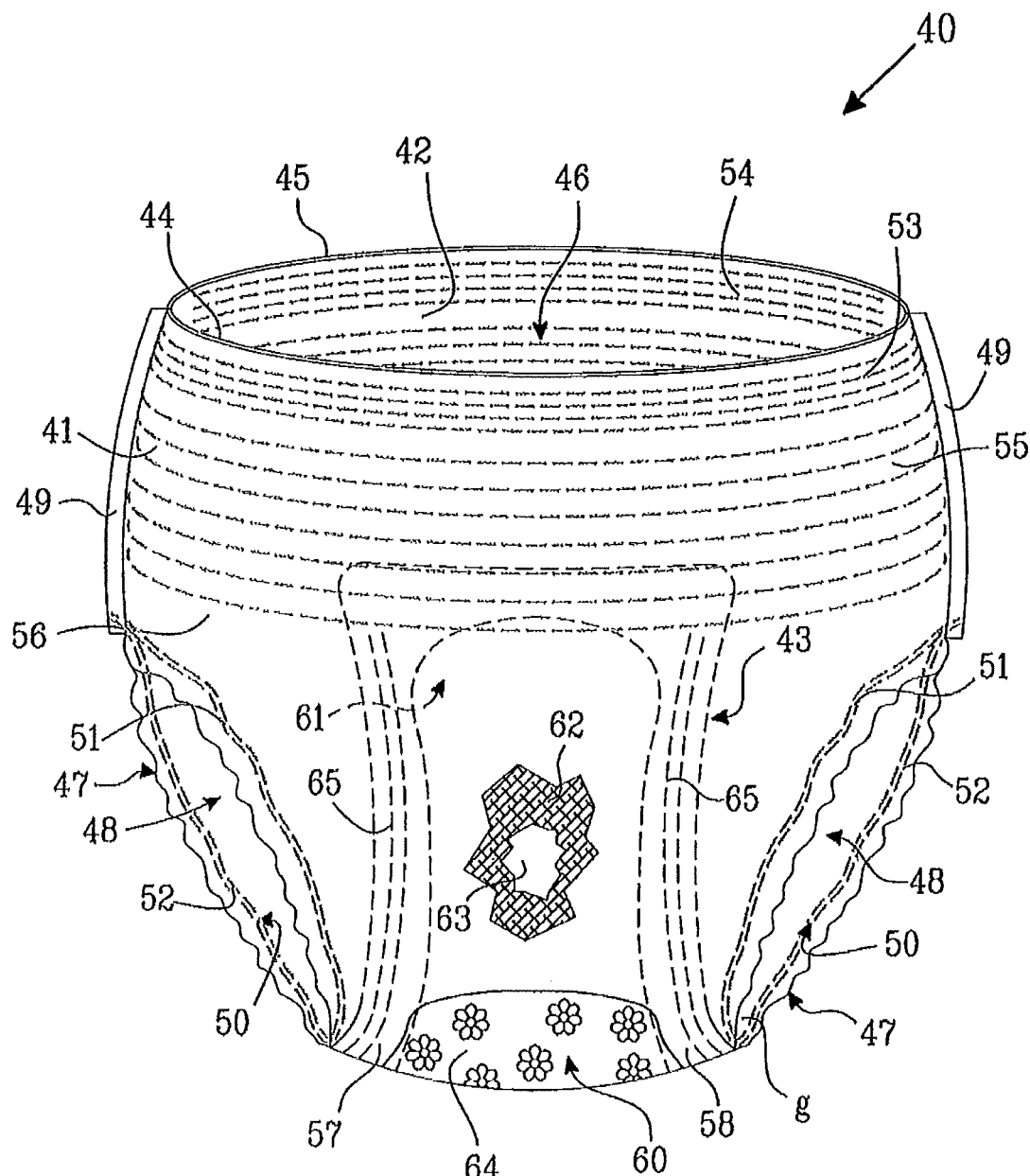
FIG. 4 shows a pant diaper made from a segment of an elasticated base web as shown in FIG. 1.

One example of a fully assembled pant garment 40 that may be produced from a base web section such as the garment sections 34 formed in the FIG. 1 process is shown in FIG. 4. The FIG. 4 garment comprises an integrated absorbent core. However, the invention is also directed to the production of chassis webs for non-absorbent or slightly absorbent pant garments.

The pant diaper 40 in FIG. 4 has a front body portion 41, a rear body portion 42 and a crotch portion 43 between the front body portion 41 and the rear body portion 42. The pant diaper 40 has front and rear waist edges 44,45 encircling a waist opening 46 and leg edges 47 encircling two leg openings 48 and side seams 49 extending between the leg openings 48 and the waist opening 46 and connecting the front body portion 41 and the rear body portion 42.

The leg openings have leg elastic 50 arranged at the leg edges 47 around the leg openings 48. Each leg elastic 50 is formed by a front elastic segment 51 and a rear elastic segment 52 which are separated by a gap, g, in the crotch portion 43. The leg elastic may be one or more elastic strings, bands, etc. as described herein.

Front and rear waist elastic 53,54 is arranged around the waist opening 46 and body elastic 55 is arranged on the front body portion 41 and the rear body portion 42 in an area between the waist elastic 53,54 and the leg openings 48. The waist elastic 53,54 may be formed by a process such as that shown in FIG. 1 or may be provided in the form of a separately produced waist band as described herein. The elastic members are arranged around the waist opening 46 in a tensioned state such that they contract and gather the nonwoven material around the waist opening 46 when they are allowed to relax, as shown in FIG. 4. A disposable pant according to the invention need not have waist elastic with the configuration shown in FIG. 4. The waist elastic may be arranged on only one of the front body portion 41 and the rear body portion 42. The waist elastic may extend along only a part of the waist opening 46 such as along a central section of the front waist edge 44 and/or the rear waist edge 45.

The body elastic 55 is shown as multiple elongated elastic members extending between the side edges 49 across the front body portion 41 and the rear body portion 42 in the area between the waist opening 46 and the leg openings 48. The elastic members may be elastic strings or bands that may be uniformly or non-uniformly spaced over the body portions 41,42 and that may have been applied with the same or different tensioning. The body elastic is not a necessary feature of the invention and may be omitted or designed in other ways as found suitable for a specific purpose. Accordingly, body elastic may be applied to only one of the front and rear body portion 41,42 and may include or consist of curved elastic elements or elastic panels formed from elastic or elasticated nonwoven material. However, in accordance with the invention, the pant diaper has no elastic elements extending across the crotch portion 43 between the leg openings 48.

The diaper 40 is formed with a chassis layer 56 extending continuously from the front waist edge 44 over the front body portion 41, through the crotch portion 43 and the rear body portion 42 to the rear waist edge 45 without any seams or joins in the chassis layer 56.

The front body portion 41 and the rear body portion 42 are connected in the crotch portion 43 by portions 57,58 of the chassis layer 56 that remain along the leg openings 48 on either side of a hole 60 in the crotch portion 43 of the chassis layer 56. The hole 60 was formed by removing portions of a base web carrying elastic elements from the crotch portion when making the pant diaper according to the method of the invention.

A core pack 61 is attached to the inside of the chassis layer 56 in the crotch portion 43. The core pack 61 comprises an absorbent core 62 being sandwiched between an inner liquid permeable topsheet 63 and an outer backsheet 64. In the pant diaper shown in FIG. 4, the backsheet 64 is exposed and visible in the crotch portion 43 through the crotch hole 60 in the chassis layer 56.

The liquid permeable topsheet 63 may consist of or comprise a layer of nonwoven material, a perforated plastic film, net material, tow, or the like. The topsheet 63 can consist of a laminate of two or more sheets of the same or different material and may have different composition or different properties within different portions of the topsheet.

The backsheet 64 may consist of a liquid-impermeable plastic film, a nonwoven sheet which has been coated with a liquid barrier material, or some other flexible sheet material having the ability to resist liquid penetration. The backsheet is preferably breathable, allowing passage of air and water vapour. As the backsheet 64 is exposed to the outside of the pant diaper in the crotch portion 43 and may come into skin contact with a wearer or caregiver when the diaper is put on and worn, the backsheet 64 may have a textile or textile-like outer surface in order to avoid the stickiness that may be felt in contact with a plastic film surface. A textile or textile-like outer surface is also preferred for the reason that it enhances the likeness of the pant diaper or other pant garments to regular underwear. In the FIG. 4 pant diaper 40, the backsheet has a flower pattern that is visible through hole 60 in the chassis layer 56. A patterned and/or textured backsheet may have a purely decorative function or may be arranged to provide a visual or tactile clue to the presence of moisture in the absorbent core 62 as described herein.

The absorption core 62 comprises absorbent material, such as absorbent fibres e.g. cellulose fluff pulp, tissue, absorbent foam, superabsorbents, absorbent composites, etc. Superabsorbents are polymer materials which are able to absorb and retain body fluid corresponding to many times their own dry weight under formation of a hydrogel. Superabsorbents are usually present in the form of particles or granules, but fibres, flakes, and films are also available. The absorption core 62 may further comprise non-absorbent components such as non-absorbent fibres, stiffening elements, shaping elements, barrier material, binders, etc. Various types of liquid-receiving porous structures such as fibre wads, open-cell foam or the like can also be included in the core.

In the pant diaper shown in FIG. 4, the core pack 61 includes side elastic 65 arranged at the side edges of the absorbent core 62. The side elastic 65 contributes to form the core into a curve shape and to form barriers against side leakage. The side elastic 65 may be applied on the core edges or may be applied outside of the core in side flaps formed from one or both of the topsheet and the backsheet to create elasticated raised barriers along the side edges of the core.

The invention claimed is:

1. A method for producing an elasticated chassis web for use as a continuous and coherent layer in a disposable pant garment, the method comprising:
 a) feeding a continuous base web along a production path in a machine direction, the continuous base web having a cross machine direction, transverse to the machine direction, and parallel side edges in the machine direction and having leg edge segments and crotch segments extending in the cross machine direction, and alternating in the machine direction;
 b) stretching first and second continuous elastic elements;
 c) feeding said first and second continuous elastic elements in said machine direction, along first and second regularly undulating wave-shaped curves, said curves having equal wave length, and having wave crests directed towards said side edges of said continuous base web and wave troughs directed away from said side edges of said continuous base web, said wave crests and wave troughs of said first wave-shaped curve being in register with said wave crests and wave troughs of said second wave-shaped curve with said elastic elements being at a maximum distance from each other within said leg edge portions of said continuous base web and with said elastic elements being at a minimum distance from each other within said crotch segments of said continuous base web;
 d) attaching said first and second stretched elastic elements to said continuous base web along said first and second regularly undulating wave-shaped curves in said leg edge segments and said crotch segments; wherein the further steps of:
 e) forming crotch cut-out pieces of said continuous base web in said crotch segments,
 f) simultaneously forming cut-off crotch segments of said stretched elastic elements being attached to said cut-out pieces of said continuous base web;
 g) creating holes in said crotch segments of said continuous base web by removing said crotch cut-out pieces from said continuous base web together with said cut-off crotch elastic segments; and
 h) covering said holes in said continuous base web by a supplementary crotch material and attaching said supplementary crotch material to an inner, wearer-facing side of said base web after cutting out and removing said crotch cut-out pieces, such that said supplementary crotch material is exposed through said holes in said continuous base web.

2. The method according to claim 1, wherein said first and second stretched elastic elements are attached to said continuous base web by means of adhesive.

3. The method according to claim 2, wherein said adhesive is applied to said continuous base web in first and second attachment areas generally coinciding with said first and second regularly undulating wave-shaped curves.

4. The method according to claim 1, wherein said first and second stretched elastic elements are covered by a covering web which is attached to said continuous base web.

5. The method according to claim 1, wherein said supplementary crotch material is in the form of discrete pieces of material.

6. The method according to claim 1, wherein said supplementary crotch material is in the form of a continuous web.

7. The method according to claim 1, wherein said crotch material has a first surface facing said continuous base web, said first surface being formed from a nonwoven material.

8. The method according to claim 1, wherein leg openings are formed in said leg edge segments of said continuous base web.

9. The method according to claim 5, wherein said supplementary crotch material is comprised in a core pack, said core pack comprising a topsheet layer, a backsheet layer and an absorbent core between said topsheet layer and said backsheet layer.

10. The method according to claim 1, wherein waist elastic is applied along at least one of said side edges of said continuous base web.

11. The method according to claim 8, wherein said continuous base web is folded along a longitudinal centre line through said base web, edge seams are formed in the cross machine direction, CD, centrally across each wave crest segment and said continuous base web is cut into individual pant garments in the cross machine direction, by cutting through said edge seams.

12. A disposable pant garment comprising:
front and rear waist edges, leg edges, a front body portion, a rear body portion and a crotch portion between said front and rear body portions, and
a coherent chassis layer extending continuously from said front waist edge to said rear waist edge and having elastic elements attached along said leg edges and along at least one of said front and rear waist edges,
said crotch portion having a hole occupying an area of said crotch portion in said chassis layer, said area of said hole being delimited by a hole periphery,
wherein said elastic elements that are attached along said leg edges terminate at said hole periphery with no part of said elastic elements extending from said hole periphery into said area of said hole, and
wherein said hole covering is covered by a supplementary crotch material which is applied on an inner, wearer-facing side of said chassis layer and is exposed through said hole in said chassis layer.

13. The disposable pant garment according to claim 12, wherein said pant garment is an absorbent pant garment.

14. The disposable pant garment according to claim 13, wherein said absorbent pant garment comprises a core pack arranged in said crotch portion, said core pack comprising a topsheet layer, a backsheet layer and an absorbent core between said topsheet layer and said backsheet layer.

15. The disposable pant garment according to claim 13, wherein said pant garment is a pant diaper having side seams connecting said front body portion with said rear body portion.

* * * * *